(12) United States Patent
Fletcher et al.

(10) Patent No.: US 10,172,742 B2
(45) Date of Patent: Jan. 8, 2019

(54) HEARING PROTECTOR WITH COMPARTMENT FOR RECHARGEABLE BATTERY PACK

(71) Applicant: 3M INNOVATIVE PROPERTIES COMPANY, St. Paul, MN (US)

(72) Inventors: Douglas D. Fletcher, Woodbury, MN (US); Oscar M. Hemberg, Dalaro (SE); Eric O. Hemberg, Shatin (HK)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/548,039

(22) PCT Filed: Jan. 27, 2016

(86) PCT No.: PCT/US2016/015037
§ 371 (c)(1),
(2) Date: Aug. 1, 2017

(87) PCT Pub. No.: WO2016/126476
PCT Pub. Date: Aug. 11, 2016

(65) Prior Publication Data
US 2018/0014972 A1 Jan. 18, 2018

Related U.S. Application Data

(60) Provisional application No. 62/110,742, filed on Feb. 2, 2015.

(51) Int. Cl.
*A61F 11/14* (2006.01)
*H04R 1/10* (2006.01)
*H04R 3/00* (2006.01)

(52) U.S. Cl.
CPC ............ *A61F 11/14* (2013.01); *H04R 1/1008* (2013.01); *H04R 1/1025* (2013.01);
(Continued)

(58) Field of Classification Search
CPC .... A61F 11/14; A61F 2011/145; A61F 11/08; A61F 11/06; A61F 2011/085;
(Continued)

(56) References Cited

U.S. PATENT DOCUMENTS

| 4,577,144 A | 3/1986 | Hodgman et al. |
| 5,212,020 A | 5/1993 | Inobe |

(Continued)

FOREIGN PATENT DOCUMENTS

| CN | 2715360 | 8/2005 |
| CN | 202103816 | 1/2012 |

(Continued)

OTHER PUBLICATIONS

"3M Occupational Health and Environmental Safety Division; High-Noise Communication Solutions", Peltor Product Brochure, 2012, pp. 1-24.

(Continued)

*Primary Examiner* — Ophelia A Hawthorne
(74) *Attorney, Agent, or Firm* — Kevin Weber

(57) ABSTRACT

A hearing protection device is provided. The hearing protection device can include a speaker to relay sounds, such as conversations, to the user of the hearing protection. The hearing protection device can be powered by a rechargeable battery pack or separately by standard batteries.

20 Claims, 5 Drawing Sheets

(52) U.S. Cl.
CPC .............. *H04R 1/1083* (2013.01); *H04R 3/00* (2013.01); *A61F 2011/145* (2013.01); *H04R 1/1041* (2013.01); *H04R 2420/09* (2013.01)

(58) Field of Classification Search
CPC .......... A61F 11/10; A61F 11/12; A61F 11/00; H04R 1/1008; H04R 1/1083; H04R 3/00; H04R 2420/09; H04R 25/60
See application file for complete search history.

(56) References Cited

U.S. PATENT DOCUMENTS

| | | | |
|---|---|---|---|
| 5,519,783 A | 5/1996 | Kumar | |
| 5,604,813 A | 2/1997 | Evans | |
| 5,729,115 A | 3/1998 | Wakefield | |
| 6,161,938 A | 12/2000 | Kish et al. | |
| 6,754,361 B1 | 6/2004 | Hall et al. | |
| 7,114,823 B2 | 10/2006 | McCullough | |
| 7,245,735 B2 | 7/2007 | Han | |
| 7,457,649 B1* | 11/2008 | Wilson ................. | H04R 1/1025 379/428.02 |
| 7,885,419 B2 | 2/2011 | Wahl | |
| 8,295,532 B2 | 10/2012 | Hsu | |
| 8,670,573 B2 | 3/2014 | Theverapperuma | |
| 2002/0003889 A1 | 1/2002 | Fischer | |
| 2005/0017673 A1 | 1/2005 | Tsukamoto et al. | |
| 2008/0069391 A1 | 3/2008 | Steyn | |
| 2008/0180874 A1* | 7/2008 | Gauger ................. | H02J 7/0055 361/235 |
| 2009/0010474 A1 | 1/2009 | Ouryouji | |
| 2009/0268935 A1 | 10/2009 | Dillinger | |
| 2009/0279711 A1 | 11/2009 | Heringslack | |
| 2010/0090654 A1 | 4/2010 | Breiting et al. | |
| 2010/0310093 A1 | 12/2010 | Semcken | |
| 2011/0142249 A1 | 6/2011 | Shinozaki | |
| 2012/0039481 A1 | 2/2012 | McClain | |
| 2013/0083927 A1 | 4/2013 | Savant | |
| 2013/0343042 A1 | 12/2013 | Windom | |
| 2013/0343591 A1 | 12/2013 | Brunner | |
| 2014/0211976 A1 | 7/2014 | Brunner | |
| 2014/0219465 A1 | 8/2014 | Saideh | |

FOREIGN PATENT DOCUMENTS

| | | |
|---|---|---|
| WO | WO 2004/027955 | 4/2004 |
| WO | WO 2008/075357 | 6/2008 |
| WO | WO 2012/009595 | 1/2012 |
| WO | WO 2013/192325 | 12/2013 |

OTHER PUBLICATIONS

"Ryobi Power Tools", Ryobi Products, [retrieved from the internet on Jul. 1. 2009], URL <https://www.ryobitools.com/power-tools/products/list/family/tek4>, pp. 1-6.
International Search Report for PCT International Application No. PCT/US2016/015037, dated Apr. 8, 2016, 2 pages.

* cited by examiner

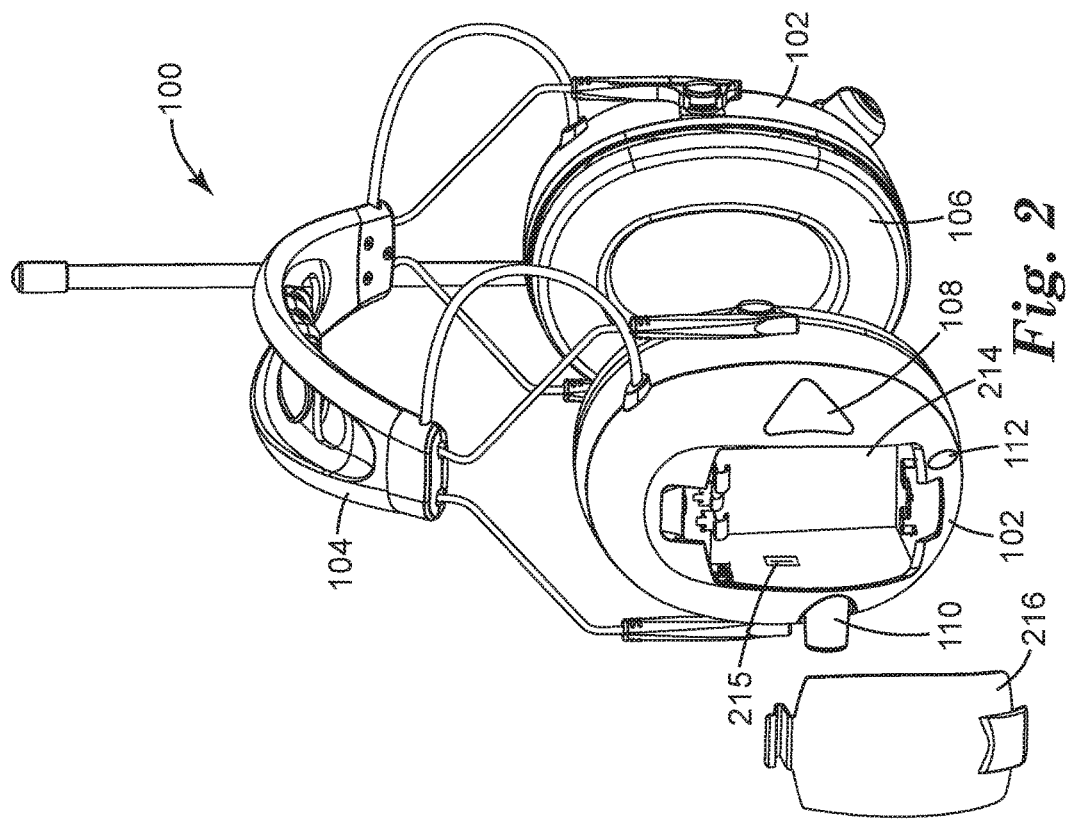
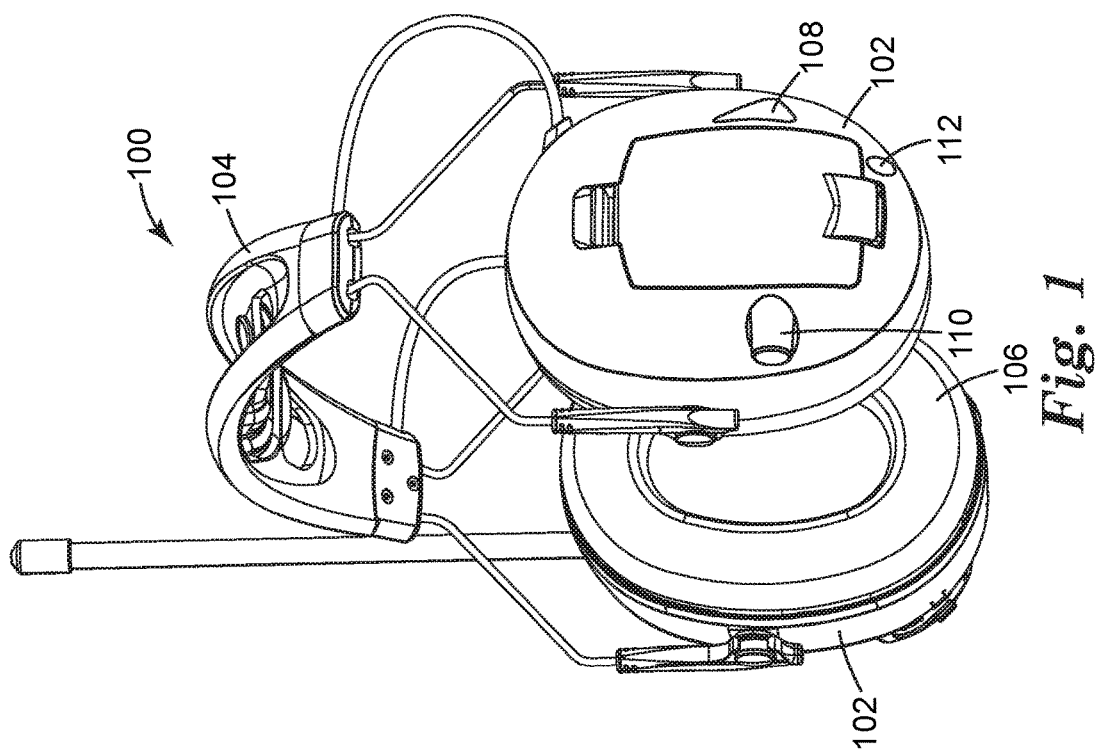

HEARING PROTECTOR WITH COMPARTMENT FOR RECHARGEABLE BATTERY PACK

CROSS REFERENCE TO RELATED APPLICATIONS

This application is a national stage filing under 35 U.S.C. 371 of PCT/US2016/015037, filed Jan. 27, 2016, which claims the benefit of provisional Application No. 62/110, 742, filed Feb. 2, 2015, the disclosure of which is incorporated by reference in its/their entirety herein.

BACKGROUND

People frequently wear hearing protection when they are in loud or noisy environments. Hearing protection can reduce the amount of noise the user's ears are exposed to. In some cases the user might want to hear some noises, such as a conversations or commands from people around them, music, other entertainment or other communication (e.g. AM/FM radio transmissions, Bluetooth transmissions, or communication from other transceivers) delivered through an input sound source. If the user is wearing hearing protection, hearing these desirable noises can be difficult or impossible. Therefore, there is a need to allow the user of hearing protection to still be able to hear some external noises, while still reducing the loud or undesirable noises.

Hearing protectors often require power to operate the apparatus. Batteries are often used to power these products. Users of hearing protection products can appreciate the convenience of using different battery types in the same apparatus. However, the different form factors of rechargeable batteries compared to standard cylindrical batteries often makes it difficult for a single apparatus to be powered by either type of battery without modifications that change the appearance and/or size of the apparatus. For safety reasons, it is also desired that products which can use rechargeable batteries have a means of preventing charging from occurring if a non-rechargeable battery or wrong type of rechargeable battery is used in the apparatus.

SUMMARY

Sound external to a hearing protection headset can be input by one or more microphones on the headset. The ambient external sound or background noises can be monitored, analyzed and filtered so that a user of the headset can better hear human voices.

In one example, an apparatus for hearing protection includes a sound input source, such as a microphone, disposed on the apparatus. The sound input source is configured to pick up an input sound wave from the environment and to convert the input sound wave to an incoming signal. The apparatus also includes a processor that is configured to receive the incoming signal and create an output signal. The apparatus can further include a speaker disposed on the apparatus. The speaker is configured to produce the output from the processor.

In one example, an apparatus for hearing protection includes a microphone disposed on the apparatus and configured to pick up an input sound wave from the environment and convert the input sound wave to an incoming signal. The apparatus also includes a processor, configured to receive the incoming signal and create an output signal. The apparatus also includes a speaker disposed on the apparatus, the speaker configured to produce the output from the processor. The apparatus also includes a battery compartment that comprises three contacts: a first positive contact configured to make electrical contact with a positive terminal of a battery or battery pack, a second negative contact configured to make electrical contact with a negative terminal of a battery or battery pack, and a third contact configured to facilitate charging of a rechargeable battery pack. The hearing protection device apparatus can be configured to prevent recharging unless there is a contact of a rechargeable battery pack making contact with the third contact. In an embodiment, the hearing protection apparatus can be powered by two standard cylindrical batteries alone, or the hearing protection device can be powered by a rechargeable battery pack alone.

One embodiment of the present disclosure is an apparatus for hearing protection comprising: two ear cups, each ear cup defining a cavity configured to fit a user's ear; a processor, configured to receive an incoming signal and create an output signal; a speaker disposed within at least one of the two ear cups, the speaker configured to produce the output from the processor; wherein one of the two ear cups comprises a battery compartment configured to house one or more batteries or battery packs, wherein the battery compartment further comprises:
   a first positive contact configured to make electrical contact with a positive terminal of one of the one or more batteries or battery packs,
   a second negative contact configured to make electrical contact with a negative terminal of one of the one or more batteries or battery packs, and
   a third contact configured to facilitate charging of a rechargeable battery pack selected from one of the one or more batteries or battery packs; and
wherein the battery compartment defines an open battery-receiving space configured to accommodate either a single rechargeable battery pack or two standard cylindrical battery shapes, wherein the apparatus further comprises a charging port, wherein the charging port is configured to receive a cable for recharging the rechargeable battery pack. In an embodiment, the apparatus is configured to prevent charging to the one or more batteries or battery packs unless there is a contact of a rechargeable battery pack contacting the third contact.

BRIEF DESCRIPTION OF THE DRAWINGS

The present disclosure may be more completely understood in connection with the following drawings, in which:

FIG. 1 is a perspective view of the headset, according to an embodiment.

FIG. 2 is a perspective view of the headset, according to an embodiment.

Figure 3:
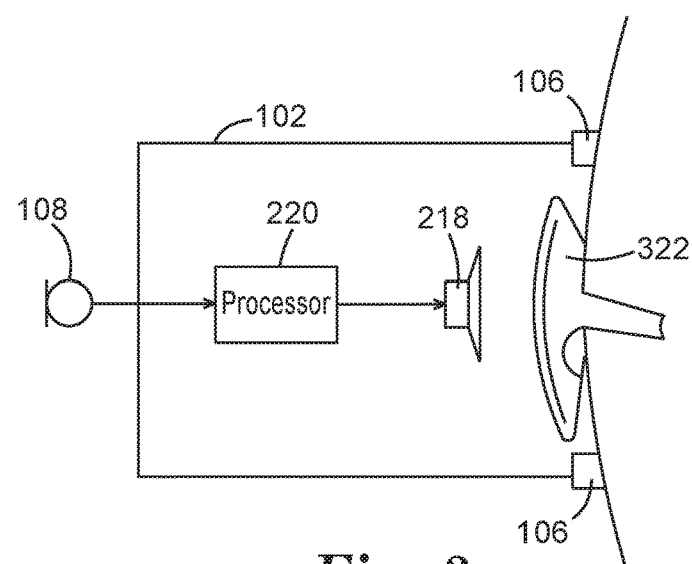
FIG. 3 is a schematic of certain headset components, according to an embodiment.

While the present disclosure is susceptible to various modifications and alternative forms, specifics thereof have been shown by way of example and drawings, and will be described in detail. It should be understood, however, that the present disclosure is not limited to the particular embodiments described. On the contrary, the intention is to cover modifications, equivalents, and alternatives falling within the spirit and scope of the present disclosure.

DETAILED DESCRIPTION

The embodiments of the present disclosure described herein are not intended to be exhaustive or to limit the present disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

FIG. 1 is a perspective view of a headset 100. In an embodiment, the headset 100 can include an ear cup 102 and a headband 104. The headset 100 can include two ear cups 102. The headband 104 can couple a first ear cup 102 with a second ear cup 102. The headband 104 can be arced, such as to extend over the top of a user's head while the headset 100 is in use. The headband 104 can be flexible, such as to allow the user to spread the first ear cup 102 from the second ear cup 102 when the user is putting on the headset 100. The headband 104 can include padding, such as to at least partially conform to the user's head and increase the user's comfort.

The ear cups 102 can be configured to fit at least partially around a user's ear, and be disposed on the side of a user's head while in use. The ear cup 102 can define a cavity. The cavity can be configured for a user's ear, a human ear, to fit within the cavity, while the user is wearing the headset 100. The ear cup 102 can include a seal ring 106. The seal ring 106 can be ring shaped, such as to extend around the user's ear. The seal ring 106 can be flexible and able to conform to the user's head. The seal ring 106 can provide a seal between the ear cup 102 and the user's head, such as to reduce the amount of noise or sound waves that reach the user's ear, thereby at least partially protecting the user's ear from external noises. The seal ring 106 can include leather, cloth, rubber, plastic, or a polymer, such as polyurethane.

The headset 100 can include a sound input source 108. In one embodiment, one or both of the ear cups 102 can include a sound input source 108. In an embodiment, the sound input source 108 can comprise a microphone. In an embodiment, there is one microphone 108 on each of two ear cups 102. In an embodiment, there can be more than one microphone 108 on one or both of the ear cups 102. In one embodiment, one or more microphones 108 are located at other locations on the headset 100. The microphone 108 can be disposed on the outside surface of the ear cup 102 opposite the cavity. The microphone 108 can pick up sound and noise from the surrounding environment. The microphone 108 can be inset, such that the microphone 108 does not extend past the outer surface of the ear cup 102. In an embodiment with two ear cups 102, each ear cup 102 can include a microphone 108. In another embodiment with two ear cups 102, only one ear cup 102 includes a microphone 108. In another embodiment with two ear cups 102, one microphone 108 is positioned on a headband portion. The noises and sounds picked up by the microphone 108 can be relayed to the user through a speaker in the cavity of the ear cup 102.

One of the ear cups 102 can include a knob 110. The user can rotate the knob 110 to control the electronics of the headset 100, such as to turn the electronics "ON" or "OFF", or to increase or decrease the volume from the speakers in the ear cups 102.

The ear cups 102 can include an input connection 112. The input connection 112 can allow a user to connect an external audio device into the headset 100, such as an AM/FM radio, a two-way radio, an MP3 player, a cellphone, or the like. The user can hear the external audio device through the one or more speakers disposed in the ear cups 102. In an embodiment, the input connection 112 can accommodate a 3.5 mm audio input. In an embodiment, an external audio device can be connected to the headset 100 through a wireless connection, such as Bluetooth connection. In an embodiment, the headset includes a Bluetooth receiver. In an embodiment, the external audio device can be built in or integral with the headset 100.

A perspective view of the headset 100 is shown in FIG. 2, from a different perspective angle than what is shown in FIG. 1. The ear cups 102 can include a battery compartment 214. The battery compartment 214 can house one or more batteries or battery packs.

As used herein, the term battery means a device consisting of one or more electrochemical cells that convert stored chemical energy into electrical energy. As used herein, the term battery pack means a set of any number of preferably identical batteries, including a single battery. A battery pack may also include other components, such as a temperature sensor or charging circuitry. A battery pack also includes a housing for containing the battery or batteries and other components.

The batteries can be used to power the electronic components of the headset 100. In an embodiment, two AA batteries can be disposed within the battery compartment 214. In an embodiment, the AA batteries can include an alkaline AA battery, a carbon AA battery, a lithium AA battery, a nickel-metal hydride AA battery, or a nickel-cadmium AA battery. In an embodiment, a rechargeable battery pack can be disposed within the battery compartment. In an embodiment, the rechargeable battery pack can use a lithium ion battery. A charging port 215 can be disposed on one or more of the ear cups. In an embodiment, the charging port can be configured to receive a cable for recharging the rechargeable battery pack. In an embodiment, the charging port is disposed on the headset in a location that permits the rechargeable battery pack to be charged while the rechargeable battery pack is inside the battery compartment. In an embodiment, the charging port is disposed on an exterior surface of the ear cup, not within the battery compartment. A battery door 216 can at least partially enclose the battery compartment 214. The battery door 216 can be configured to be removed from the headset 100 when access to the batteries are desired, such as to replace the batteries. In an embodiment, the compartment door can fully enclose the batteries or battery pack within the battery compartment without protruding above the adjacent outer surfaces of ear cup 102. In embodiments, the battery compartment door protrudes no more than 5 millimeters above adjacent outer surfaces of the ear cup when the battery compartment houses the one or more batteries or battery pack and the battery compartment door is closed. The battery compartment door can comprise a hinge. In an embodiment, the battery door 216 is a separate element from the batteries or battery packs. In an embodiment, the battery door is a separate element from the remainder of the headset 100.

Each ear cup 102 can include a speaker 218, shown in FIG. 3. The speaker 218 can produce an output, such as a sound wave. Incoming sound and noise from sound input 108 can be input into a processor 220 and be processed, such as to eliminate at least some of the noise, to produce an output through the speaker 218. As used herein, the term sound refers to desirable audio information while the term noise refers to undesirable audio information. The speaker 218 can provide sound to the user, such as desirable audio. Desirable audio can include conversations, commands, warnings or other communications, such as communications between two people. The input from each microphone can be processed to eliminate at least some of the noise, such as undesirable noises. Undesirable noises can include mechanical noises, noises from ventilation systems, distant conversations, impulse noises, grinding, squeaking, engine noises, gun shots, explosions and the other similar noises.

The headset 100 can include digital electronic components, analog electronic components or a mix of both types.

The speaker 218 can relay sounds from the surrounding environment picked up by the sound input 108. The speaker 218 can relay sounds from an external audio device connected from the input connection 112. The output from the speaker 218 can be limited to a maximum output level, such as to protect the user's ears. In different embodiments, the maximum output level from the speaker 218 due to sound from the microphone can be at least 80 dB(A), not more than 90 dB(A), at least 70 dB(A), not more than 100 dB(A), and combinations of these constraints. In an embodiment, the output from the speaker 218 is limited to 82 dB(A) when the ambient sound level is less than 106 dB(A), regardless of how high the user has the volume turned up. In an embodiment, the output from the speaker 218 is limited to 85 dB(A) when the ambient sound level is less than 106 dB(A), regardless of how high the user has the volume turned up. In an embodiment, the output from the speaker 218 is limited to 82 dB(A), regardless of how high the user has the volume turned up. In an embodiment, the output from the speaker 218 is limited to 85 dB(A), regardless of how high the user has the volume turned up. In an embodiment, the output from the speaker 218 can be limited to 82 dB(A) when an external audio device is connected to the input connection 112. The sounds picked up by the microphone 108 can be processed before they are produced as output from the speaker 218. The processing can increase the quality or clarity of what the user hears, such as by reducing background noise, suppressing impulse noises or keeping an input level constant. In one embodiment where each of two ear cups 102 has a microphone 108, the incoming sound and noise is processed by a single processor. In another embodiment where each of the two ear cups 102 has a microphone 108, the incoming sound and noise is processed by separate processors.

The individual features described herein can be present in various embodiments. Also combinations of the individual features described herein can be present in various embodiments. In an embodiment, a hearing protection apparatus can include a battery compartment that comprises three contacts: a first positive contact configured to make electrical contact with a positive terminal of a battery or battery pack, a second negative contact configured to make electrical contact with a negative terminal of a battery or battery pack, and a third contact configured to facilitate charging of a rechargeable battery pack. The hearing protection device apparatus can be configured to prevent recharging unless there is a contact of a rechargeable battery pack making contact with the third contact. In an embodiment, the hearing protection apparatus can be powered by two standard cylindrical batteries alone, or the hearing protection device can be powered by a rechargeable battery pack alone.

The hearing protection apparatus comprises a battery compartment that is configured to house one or more batteries or battery packs. The user has the option to power the apparatus with either a rechargeable battery pack alone or two standard cylindrical batteries alone as the power source; the battery compartment is configured to secure either power source within the compartment. The ability to use standard cylindrical batteries provides users with a power option that is readily available in commercial outlets and inexpensive to purchase. The ability to use a rechargeable battery pack carries many benefits also, including longer use times and lower operational costs than standard batteries can provide. The ability for the rechargeable battery pack to be recharged by charging circuitry built into the hearing protection apparatus lowers a user's costs by not requiring an external charger unit. In some embodiments, the rechargeable battery pack can be substituted for the standard cylindrical batteries within the same battery compartment, where the same battery compartment door is able to close over the rechargeable battery pack as over the standard cylindrical batteries.

Figure 4:
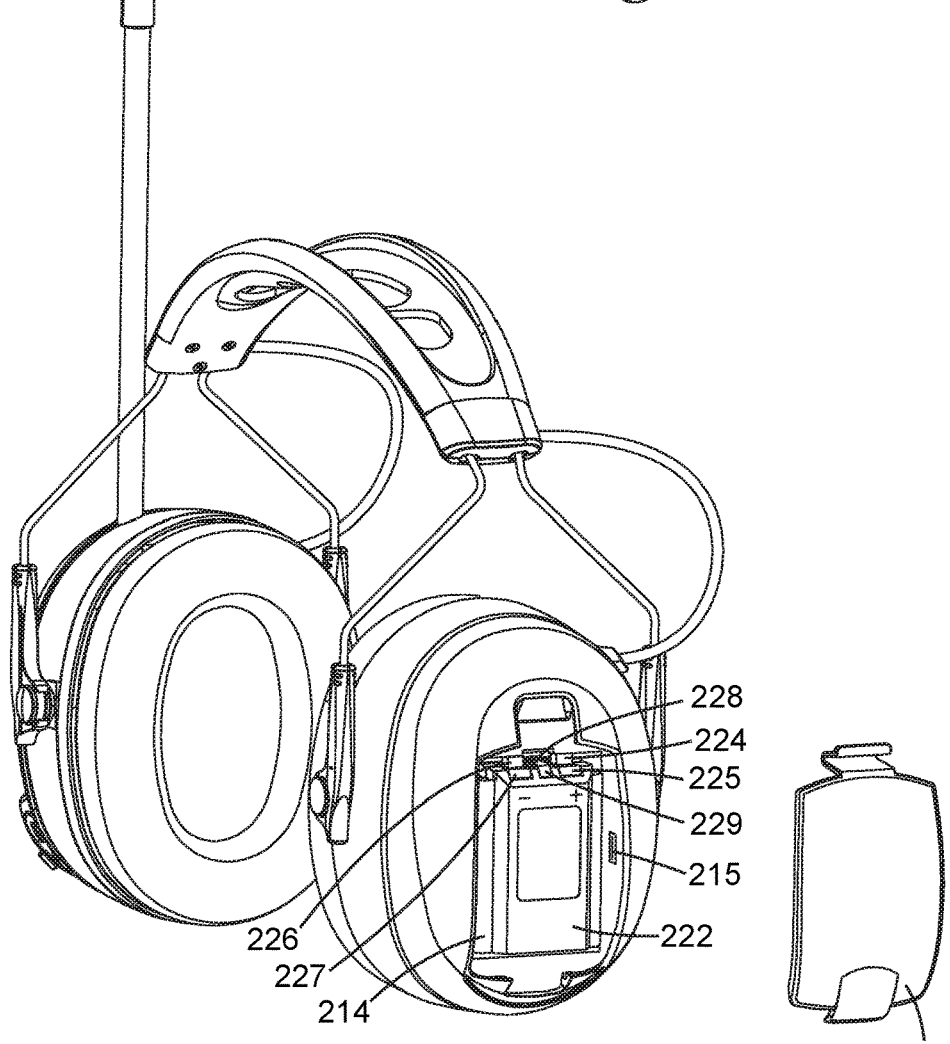
FIG. 4 is a perspective view of a headset embodiment with a rechargeable battery pack, according to an embodiment.
Figure 5:
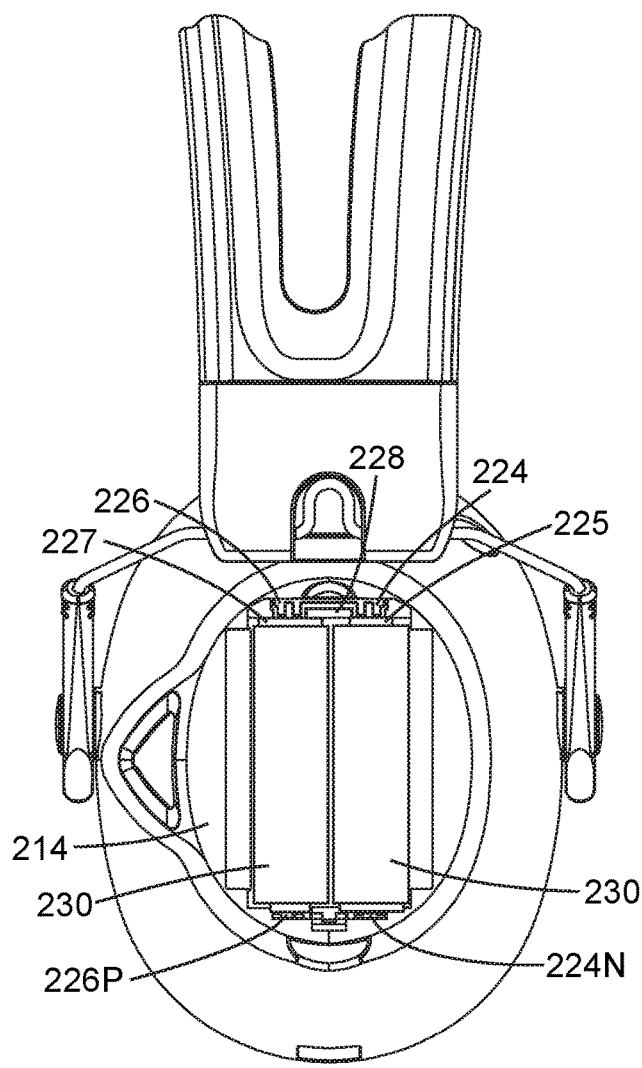
FIG. 5 is a perspective view of the headset with two standard batteries, according to an embodiment.

FIG. 4 and FIG. 5 show embodiments of the apparatus where different types of batteries or battery packs are used to provide power to the apparatus. In FIG. 4, a rechargeable battery pack 222 is disposed in the battery compartment 214. The rechargeable battery pack has contact 225 for its positive terminal that makes contact with positive contact 224 of the battery compartment, and the rechargeable battery pack has a contact 227 for its negative terminal that makes contact with negative contact 226 of the battery compartment. In addition, the rechargeable battery pack also includes a third contact 229 which contacts a third contact 228 of the battery compartment that is configured to facilitate recharging of the rechargeable battery pack. There are many different options for how the third contact can facilitate recharging of the battery pack, as will be described herein. In an embodiment, the third contact 228 in the battery compartment is electrically connected to charging port 215. FIG. 4 also shows compartment door 216 which can fully enclose rechargeable battery pack 222 within the battery compartment.

FIG. 5 shows the battery compartment 214 with two AA batteries 230 used to power the apparatus instead of the rechargeable battery pack. One battery has a contact 225 on one end for a positive terminal that makes contact with positive contact 224 of the battery compartment, and one battery has a contact 227 on one end for a negative terminal that makes contact with negative contact 226 of the battery compartment. Additional positive terminal 226P and negative terminals 224N are disposed on the battery compartment to make contact with the opposite end of each battery. When two AA batteries are used instead of the rechargeable battery pack, there is no contact on either of the AA batteries that makes contact with third contact 228 of the battery compartment. The batteries 230 cannot be recharged in the apparatus because they do not make contact with third contact 228.

Figure 6:
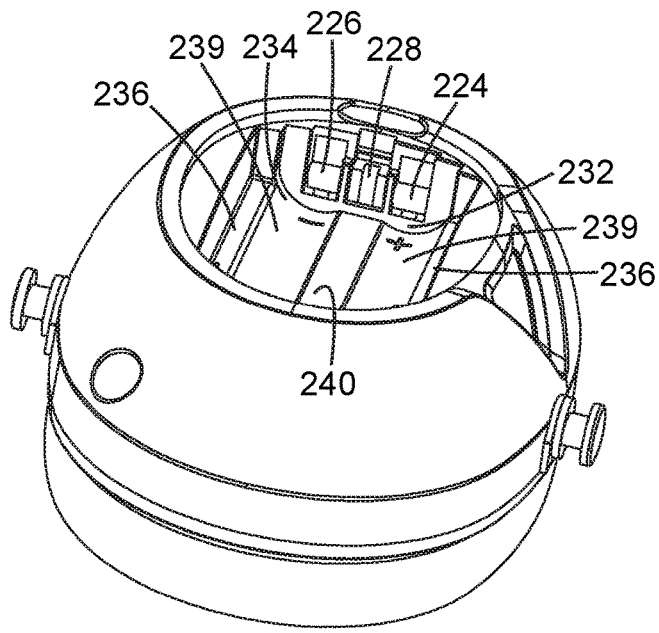
FIG. 6 is a perspective view of the empty battery compartment of the headset, according to an embodiment.

FIG. 6 shows a perspective of the battery compartment 214 without any batteries or battery packs inside it. First contact 224, a positive contact configured to make electrical contact with a positive terminal, second contact 226, a negative contact configured to make electrical contact with a negative terminal, and third contact 228 can be seen in the figure. In an embodiment, third contact 228 is configured to make electrical contact with a positive charging contact of a rechargeable battery pack. In an embodiment, third contact 228 is configured to make electrical contact with a negative charging contact of a rechargeable battery pack. In such embodiments, the third contact is electrically connected to a charging port within the housing of the headset or an ear cup of the apparatus. The electrical connection of the third contact with the charging port may be via some circuitry. In an embodiment, the third contact is electrically connected to a charging port, wherein the charging port is located somewhere on the headset, and charging of the rechargeable battery pack occurs through a circuit that includes the third contact 228 and either the first positive contact 224 or the second negative contact 226. In an embodiment, charging to the one or more battery packs occurs through either a circuit that includes the third contact and the first positive contact and excludes the second negative contact or a circuit that includes the third contact and the second negative contact and excludes the first positive contact.

The third contact 228 can also be connected to other systems or devices for monitoring or protecting the rechargeable battery in the battery pack. In an embodiment, these systems or devices can be in the rechargeable battery pack. In other embodiments, these systems or devices are within the housing of the headset or an ear cup of the apparatus. In an embodiment, portions of these systems or devices are in the rechargeable battery pack and portions of these systems or devices are within the housing of the headset or an ear cup of the device.

In an embodiment, the third contact is configured to make electrical contact with a temperature monitoring device. In such embodiments, the apparatus could prevent current from flowing or issue a warning to the user if the temperature of the battery pack approaches an unsafe level. In one embodiment, the battery pack includes a temperature sensor while the headset includes a temperature monitoring circuit that receives input from the temperature sensor via the third contact.

In embodiments, the third contact 228 can be configured to make contact with an identification device or circuit within the headset and rechargeable battery pack. In such embodiments, the identification circuit is configured to identify if an improper battery type is placed into the compartment and prevent current flow in the apparatus, issue a warning to the user or both. The identification circuit could prevent or allow current flow based on an electrical connection to the third contact of the rechargeable battery pack. Alternatively, or in addition, the identification device could prevent or allow current flow based on a mechanical connection to the third contact of the rechargeable battery pack. In alternative embodiments, such as where a mechanical connection to the third contact provides the indication that the correct rechargeable battery is in the compartment, the identification device could be located entirely within the headset.

The charging port 215 can also be electrically connected to the first positive contact 224 and the second negative contact 226 with the third contact 228 being electrically connected to a device or system that controls the charging circuit, such as an identification device, a monitoring device, or other control device. In such embodiments, charging can only occur if a rechargeable battery pack also has a separate contact that is electrically connected to the third contact 228. In an embodiment, the charging circuit is electrically connected to the first positive contact and the second negative contact, and the third contact is electrically connected to an identification device within the rechargeable battery pack. In an embodiment, the charging port is electrically connected to the first positive contact and the second negative contact, and the charging of the rechargeable battery pack occurs through a circuit that includes the first positive contact and the second negative contact. In an embodiment, the charging circuit is electrically connected to the first positive contact and the second negative contact, the third contact is electrically connected to an identification or a protection device within the rechargeable battery pack, and the charging of the rechargeable battery pack occurs through a circuit that includes the first positive contact and the second negative contact. In an embodiment, the identification system is located within the rechargeable battery pack. In other embodiments, the identification system or device is located within the housing of the headset or an ear cup of the apparatus. In an embodiment, portions of the identification system are located in the rechargeable battery pack and portions of the identification systems are located within the housing of the headset or an ear cup of the device.

The battery compartment 214 defines an open battery-receiving space wherein the space includes a first region 232 having at least a portion of the first region adjacent to the first positive contact 224, a second region 234 having at least a portion of the second region adjacent to the second negative contact 226, and a third region 236, the third region at least partially overlapping both the first region and the second region; wherein the first, second, and third regions together are configured to accommodate either a single rechargeable battery pack or two standard cylindrical battery shapes. In an embodiment, the third region is wider than double the diameter of the standard cylindrical battery shape. The battery compartment can accommodate the form factors of different batteries or battery packs. First region 232 and second region 234 are cylindrical regions that are defined by portions of the battery compartment that include curved surfaces that can help secure at least a portion of the one or more batteries or rechargeable battery pack against the battery compartment. The curved surfaces may comprise portions of cylindrical shapes that conform to an outside surface of a standard cylindrical battery. In an embodiment, the battery compartment surfaces may define one or more curved surfaces, adjacent to the positive and negative contacts of the battery compartment, that are configured to secure the batteries or battery packs against the compartment. The battery compartment can comprise a bottom surface having at least a first curved surface and a second curved surface, wherein the first curved surface is adjacent to the first positive contact of the battery compartment and the second curved surface is adjacent to the second negative contact of the battery compartment. In embodiments, a bottom surface of the battery compartment may comprise one or more curved surfaces that bound at least a portion of the first and second regions.

In an embodiment, the curved surfaces 239 on the bottom surface of the battery compartment may extend below an adjacent flat section 240 disposed on the bottom surface of the battery compartment. The width of the flat section 240 can vary depending on the desired spacing between the cylindrical batteries. One curved surface is also adjacent to positive contact 224 and the other curved section is also adjacent to negative contact 226. The curved surfaces can extend from 0.5 to 3-mm below the flat section, or 1 to 2 mm below the flat section. In other embodiments, a top surface of the battery compartment may comprise one or more curved surfaces that bound at least a portion of the first and second regions. In an embodiment, the curved surfaces on the top surface of the battery compartment may extend above an adjacent flat section disposed on the top surface of the battery compartment. One curved surface is also adjacent to a positive contact and the other curved surface is also adjacent to a negative contact. The curved surface can extend from 0.5 to 3-mm above the flat section, or 1 to 2 mm above the flat section. In an embodiment, the thickness of the rechargeable battery pack is less than the diameter of a standard cylindrical battery shape. Though curved surfaces are present in some embodiments, other embodiments do not include any curved surfaces in the battery compartment.

The rechargeable battery pack can comprise a protection monitoring circuit (PMC) which protects the rechargeable battery from different conditions that may occur during use, including overcharging, over discharging, overcurrent, and load short circuiting. In an embodiment, the protection monitoring circuit in the rechargeable battery pack makes electrical contact with the third contact 228 in the battery compartment. In an embodiment, the protection monitoring circuit is configured to make electrical contact with the third contact 229 of the rechargeable battery pack. The PMC can include aspects of the identification circuit and temperature monitoring circuit described herein.

Figure 7:
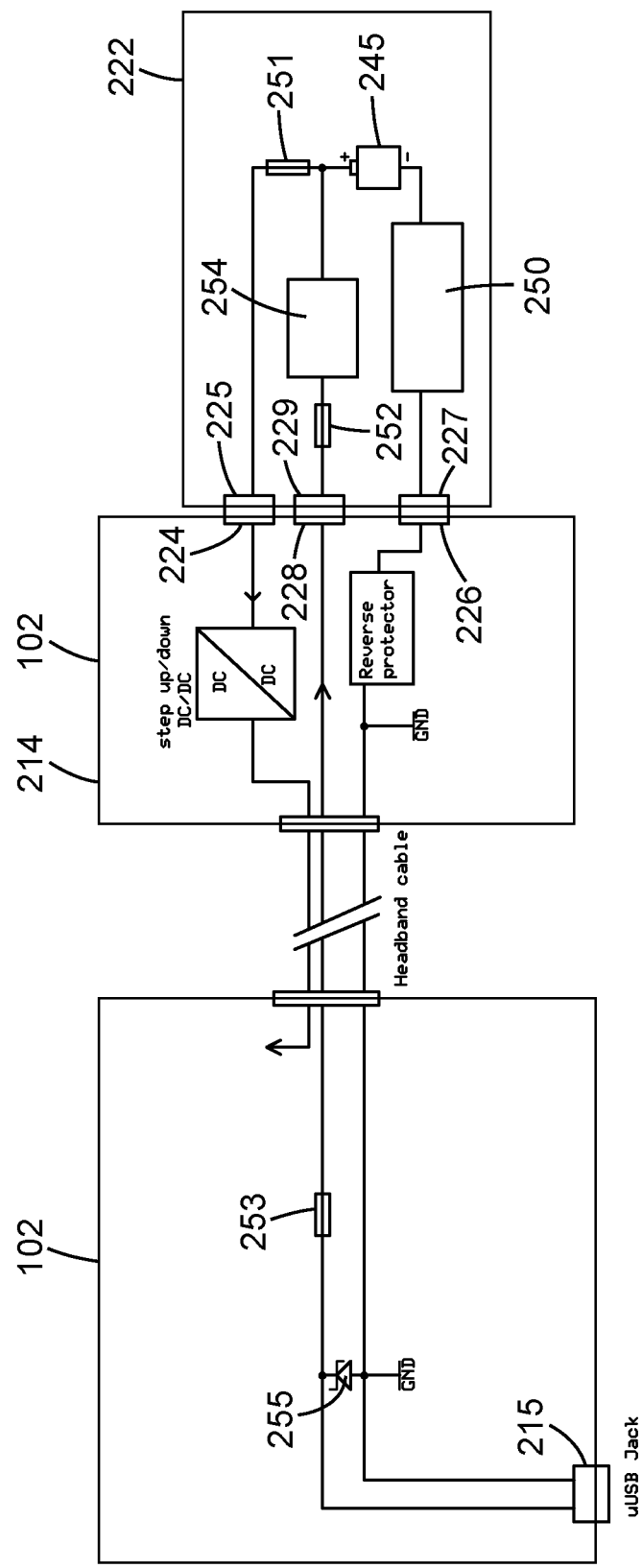
FIG. 7 is a schematic diagram of certain elements of a rechargeable battery pack and hearing protector, according to an embodiment.

FIG. 7 shows elements of a schematic design for the rechargeable battery pack and headset using a protection monitoring circuit. The rechargeable battery pack 222 comprises a lithium ion cell 245 that has a positive terminal 225 connected to contact 224 and a negative terminal 227 connected to contact 226. The rechargeable battery pack also includes third contact 229. When the rechargeable battery is positioned in the battery compartment 214, then the first contact 225, second contact 227 and third contact 229 of the rechargeable battery pack 222 are in contact with the first contact 224, second contact 226 and third contact 226 of the battery compartment 214. The battery compartment 214 is located in one of the ear cups 102, which is electrically connected to the other ear cup 102 by a headband cable. In an embodiment, the rechargeable battery pack 222 includes a charger circuit 254 and a protection monitoring circuit 250. In the embodiment of FIG. 7, the third contact 228 of the battery compartment is electrically connected to the charging port 215 in the opposite ear cup 102 by the headset cable. Additional elements including fuses 251, 252, and 253 and diodes 255 can be included to work in conjunction with the PMC 250 and the charger circuit 254 to provide protection and recharging functions to the rechargeable battery and the headset.

Figure 8:
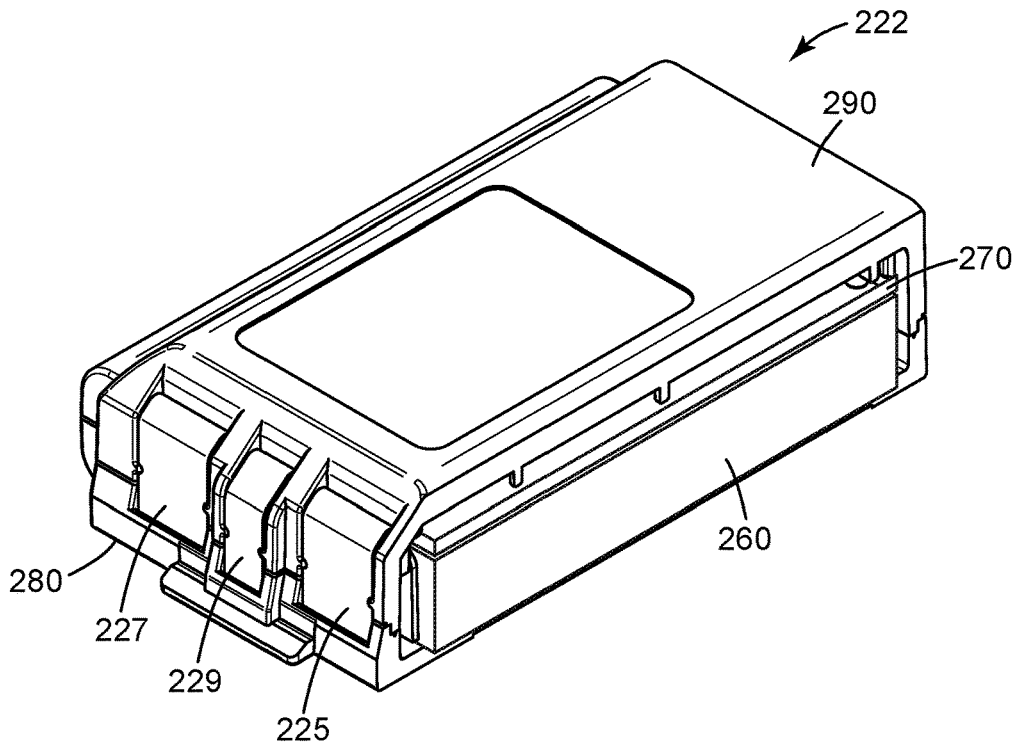
FIG. 8 is a perspective cut-away view of a rechargeable battery pack of FIG. 7, according to an embodiment.

A perspective cut-away view of an embodiment of the rechargeable battery pack is shown in FIG. 8. In FIG. 8, the rechargeable battery pack 222 can include a lithium ion cell 260 and a printed circuit board 270 containing circuitry that is configured to control the charging and protection functions of the battery pack. The circuitry on the printed circuit board 270 can also be configured to control temperature monitoring and identification functions as well. The battery pack includes a top surface 280 and a bottom surface 290. In FIG. 8, the lithium ion battery is positioned towards the top portion of the battery pack. In other embodiments, the lithium ion battery can be positioned towards the bottom portion of the battery pack, from the perspective of FIG. 8. In FIG. 8, the rechargeable battery pack has contact 225 for its positive terminal that makes contact with a positive contact of the battery compartment, and the rechargeable battery pack has a contact 227 for its negative terminal that makes contact with a negative contact of the battery compartment. In addition, the rechargeable battery pack also includes a third contact 229 which contacts a third contact of the battery compartment that is configured to facilitate recharging of the rechargeable battery pack. The third contact may be disposed on the same surface of the rechargeable battery pack as the contacts for the positive and negative terminals are disposed on, or the third contact may be disposed on a surface that extends from the surface that the contacts for the positive and negative terminals are disposed on. In embodiments, the third contact could be recessed from the contacts for the positive and negative terminals.

Figure 9A:
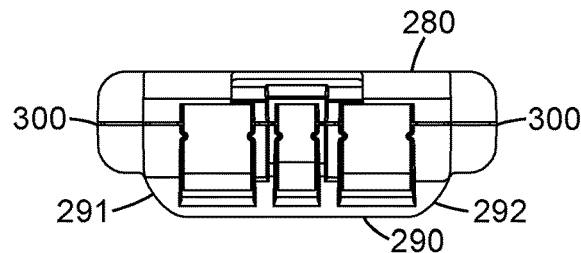
FIG. 9a is a perspective view of a rechargeable battery pack, according to an embodiment.
Figure 9B:
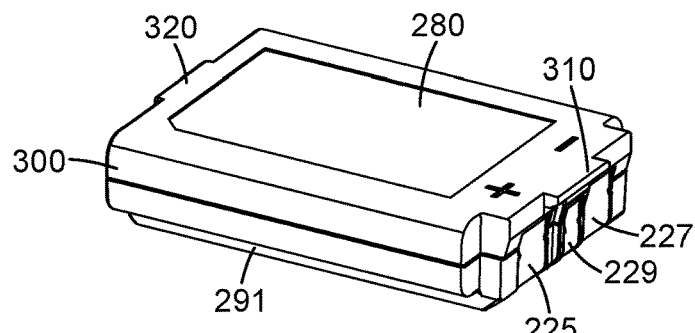
FIG. 9b is a perspective view of a rechargeable battery pack, according to an embodiment.

Additional features for the shape of the rechargeable battery pack are shown in FIG. 9a and FIG. 9b. The shape features of the rechargeable battery pack can be used to secure the rechargeable battery pack inside the battery compartment.

A perspective view of the rechargeable battery pack is shown in FIG. 9a. The rechargeable battery back includes top surface 280, bottom surface 290, curved portions 291 and 292, and sides 300. The top surface 280 is wider than the bottom surface 290, and sides 300 extend past curved portions 291 and 292 in order to accommodate the rechargeable battery positioned towards the top portion of the pack in this embodiment. When installed in the battery compartment, curved portions 291 and 292 are secured against the battery compartment in the first and second regions of the battery compartment so that the rechargeable battery pack stays in place during recharging and use. At least a portion of the bottom surface 290 is also secured against the battery compartment. Portions of the top surface 280 and sides 300 are secured against the battery compartment in the third region. FIG. 9b also shows extensions 310 and 320. In an embodiment, the extension 310 and 320 are configured to secure one or more portions of the rechargeable battery pack against the battery compartment. Extensions can be included on any side or surface of the rechargeable battery pack to help secure the rechargeable battery pack against the battery compartment. Such extensions can be useful when the length, width, and height dimensions of a rechargeable battery in the battery pack are different from the length, width, and height dimensions of standard cylindrical batteries. In an embodiment, extensions protrude from the sides 300 of the battery pack to secure one or more portions of the rechargeable battery pack against the battery compartment. In other embodiments, the extensions can protrude from one or more of the top, bottom, or side surfaces of the rechargeable battery pack.

In an embodiment, at least a portion of the third contact 229 may be disposed on at least a portion of extension 310. The extensions 310 can extend 0.5 to 3 mm from the surfaces or sides of the rechargeable battery pack, more preferably from 1-2 mm.

The apparatus can use different batteries or battery packs as power sources. When standard cylindrical battery shapes are used, the apparatus can operate on AA-sized or AAA-sized batteries. The standard cylindrical batteries can be rechargeable or non-rechargeable batteries. However, in an embodiment, the apparatus will not recharge standard cylindrical rechargeable batteries. A typical AA battery measures 49.2 to 50.5 mm in length, including the button terminal, and 13.5 to 14.5 mm in diameter. The positive terminal button contact can be about 1 mm high and about 5.5 mm in diameter. The flat negative terminal contact can be about 7 mm in diameter. Examples of cylindrical batteries that can be used include alkaline AA batteries, carbon AA batteries, non-rechargeable lithium AA batteries, rechargeable nickel-metal hydride AA batteries, and rechargeable nickel-cadmium AA batteries. The voltage of the AA batteries that can be used in the apparatus can be between 1 and 2 V, preferably between 1.1 and 1.6 V. When a rechargeable battery pack is used to power the apparatus, the rechargeable battery pack can comprise a rechargeable lithium-ion battery, a lithium-polymer battery, or other rechargeable battery. The voltage provided by the rechargeable battery can be between 2.5 to 5 V, preferably 3 to 4 V.

The rechargeable battery pack can have several different shapes, depending on the desired dimensions of the space defined in the battery compartment. The rechargeable battery pack can have an overall width no more than 38 mm, no more than 42 mm, or no more than 50 mm. The rechargeable battery pack can have an overall width no less than 25 mm, no less than 28 mm, or no less than 35 mm. The rechargeable battery pack can have an overall length no more than 55 mm, no more than 52 mm, or no more than 46 mm. The rechargeable battery pack can have an overall length no less than 35 mm, no less than 40 mm, or no less than 45 mm. The rechargeable battery pack can have an overall thickness no more than 20 mm, no more than 16 mm, or no more than 14 mm. The rechargeable battery pack can have an overall thickness no less than 8 mm, no less than 10 mm, or no less than 15 mm.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this present disclosure pertains. All publications and patent applications are herein incorporated by reference to the same extent as if each individual publication or patent application was specifically and individually indicated by reference.

The present disclosure has been described with reference to various specific and preferred embodiments and techniques. However, it should be understood that many variations and modifications may be made while remaining within the spirit and scope of the present disclosure.

We claim:

1. An apparatus for hearing protection, comprising:
   two ear cups, each ear cup defining a cavity configured to fit a user's ear;
   a processor, configured to receive an incoming signal and create an output signal;
   a speaker disposed within at least one of the two ear cups, the speaker configured to produce the output from the processor;
   wherein one of the two ear cups comprises a battery compartment configured to house one or more batteries or battery packs, wherein the battery compartment further comprises:
   a first positive contact configured to make electrical contact with a positive terminal of one of the one or more batteries or battery packs,
   a second negative contact configured to make electrical contact with a negative terminal of one of the one or more batteries or battery packs, and
   a third contact configured to facilitate charging of a rechargeable battery pack selected from one of the one or more batteries or battery packs; and
   wherein the battery compartment defines an open battery-receiving space configured to accommodate either a single rechargeable battery pack or two standard cylindrical battery shapes,
   wherein the apparatus further comprises a charging port, wherein the charging port is configured to receive a cable for recharging the rechargeable battery pack.

2. The apparatus of claim 1 wherein the wherein the battery-receiving space comprises:
   a first region having at least a portion of the region adjacent to the first positive contact,
   a second region having at least a portion of the region adjacent to the second negative contact, and
   a third region, the third region at least partially overlapping both the first region and the second region; and
   wherein the first, second, and third regions together are configured to accommodate either a single rechargeable battery pack or two standard cylindrical battery shapes.

3. The apparatus of claim 2, wherein the third region has a width wider than double a diameter of the standard cylindrical battery shape.

4. The apparatus of claim 2 wherein the first and second regions of the battery compartment are adapted to be located closer to the user's head when worn than the third region.

5. The apparatus of claim 2 wherein the third region of the battery compartment is adapted to be located closer to the user's head when worn than the first and second regions.

6. The apparatus of claim 1 wherein the apparatus is configured to prevent charging to the one or more batteries or battery packs unless there is a contact of a rechargeable battery pack contacting the third contact.

7. The apparatus of claim 6 wherein charging to the one or more batteries or battery packs occurs through either a circuit that includes the third contact and the first positive contact and excludes the second negative contact or a circuit that includes the third contact and the second negative contact and excludes the first positive contact.

8. The apparatus of claim 6 wherein charging to the one or more batteries or battery packs occurs through a circuit that includes the first positive contact and the second negative contact.

9. The apparatus of claim 1 wherein the third contact is configured to make electrical contact with a positive charging contact of a rechargeable battery pack selected from one of the one or more batteries or battery packs.

10. The apparatus of claim 9 wherein the third contact is electrically connected to the charging port.

11. The apparatus of claim 9 further comprising a fuse and a charging device wherein the third contact is electrically connected to the fuse and charging device.

12. The apparatus of claim 1 wherein the battery compartment is at least partially enclosed by a battery compartment door.

13. The apparatus of claim 12 wherein the battery compartment door protrudes no more than 5 millimeters above adjacent outer surfaces of the ear cup when the battery compartment houses the one or more batteries or battery pack and the battery compartment door is closed.

14. The apparatus of claim 1 wherein the battery compartment further comprises a bottom surface having at least a first curved surface and a second curved surface, wherein the first curved surface is adjacent to the first positive contact of the battery compartment and the second curved surface is adjacent to the second negative contact of the battery compartment.

15. The apparatus of claim 1 wherein the standard cylindrical battery shape is a standard AA battery shape or a standard AAA battery shape.

16. The apparatus of claim 1 further comprising a temperature monitoring device wherein the third contact is electrically connected to the temperature monitoring device.

17. The apparatus of claim 1 further comprising an identification device wherein the third contact is configured to make contact with an identification device.

18. The apparatus of claim 1 further comprising the rechargeable battery pack, wherein the rechargeable battery pack comprises a lithium ion cell.

19. The apparatus of claim 1 further comprising a standard cylindrical battery, wherein the standard cylindrical battery comprises an alkaline AA battery, a carbon AA battery, a lithium AA battery, a nickel-metal hydride AA battery, or a nickel-cadmium AA battery.

20. The apparatus of claim 1 further comprising a microphone disposed on the apparatus, the microphone configured to pick up an input sound wave from the environment and convert the input sound wave to an incoming signal.

* * * * *

UNITED STATES PATENT AND TRADEMARK OFFICE
CERTIFICATE OF CORRECTION

PATENT NO. : 10,172,742 B2  
APPLICATION NO. : 15/548039  
DATED : January 8, 2019  
INVENTOR(S) : Fletcher et al.

Page 1 of 1

It is certified that error appears in the above-identified patent and that said Letters Patent is hereby corrected as shown below:

In the Claims

Column 12
Line 22, Claim 2, delete "wherein the wherein the" and insert -- wherein the --, therefor.

Signed and Sealed this
Tenth Day of September, 2019

Andrei Iancu
*Director of the United States Patent and Trademark Office*